(12) United States Patent
Bulman

(10) Patent No.: US 12,263,086 B2
(45) Date of Patent: Apr. 1, 2025

(54) COMBINED INTRODUCER AND EXPANDABLE SHEATH

(71) Applicant: Edwards Lifesciences Corporation, Irvine, CA (US)

(72) Inventor: Erik Bulman, Lake Forest, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 801 days.

(21) Appl. No.: 17/342,866

(22) Filed: Jun. 9, 2021

(65) Prior Publication Data

US 2021/0290376 A1   Sep. 23, 2021

Related U.S. Application Data

(63) Continuation of application No. PCT/US2019/064875, filed on Dec. 6, 2019.

(60) Provisional application No. 62/778,698, filed on Dec. 12, 2018.

(51) Int. Cl.
*A61F 2/24* (2006.01)

(52) U.S. Cl.
CPC ...... *A61F 2/243* (2013.01); *A61F 2210/0057* (2013.01); *A61F 2250/001* (2013.01)

(58) Field of Classification Search
CPC ........ A61F 2210/0057; A61F 2250/001; A61F 2/243; A61F 2/962
See application file for complete search history.

(56) References Cited

U.S. PATENT DOCUMENTS

| | | | |
|---|---|---|---|
| 519,297 | A | 5/1894 | Bauer |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |

(Continued)

FOREIGN PATENT DOCUMENTS

| DE | 19532846 A1 | 3/1997 |
|---|---|---|
| DE | 19907646 A1 | 8/2000 |

(Continued)

*Primary Examiner* — Suzette J Gherbi
(74) *Attorney, Agent, or Firm* — Meunier Carlin Curfman LLC; Joel B. German

(57) ABSTRACT

Disclosed herein is a combined introducer and expandable sheath having an inner member and an outer elastomeric jacket. The inner member has radially folded tapered segments in an unexpanded state that are mechanically unfolded and moved toward the inner wall of the elastomeric jacket by a medical device moving through the lumen of the inner member. The compressive outer elastomeric jacket returns the expanded inner member back to the radially folded, unexpanded state once the medical device has passed through the expanded lumen of the inner member. The structure can include a distal region that tapers to a rounded tip. The proximal region also tapers to mate with a hemostasis value housing.

28 Claims, 5 Drawing Sheets

(56) References Cited

U.S. PATENT DOCUMENTS

| | | |
|---|---|---|
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,944,690 A | 8/1999 | Falwell et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 10,912,919 B2 * | 2/2021 | Bulman ............ A61M 25/0662 |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0087968 A1 | 5/2004 | Core |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0004555 A1 * | 1/2005 | Pursley ............ A61M 25/0152 |
| | | 604/528 |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0103520 A1 | 5/2008 | Selkee |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123529 A1 | 5/2012 | Levi et al. |
| 2012/0239142 A1 | 9/2012 | Liu et al. |
| 2013/0030519 A1 | 1/2013 | Tran et al. |
| 2013/0317598 A1 | 11/2013 | Rowe et al. |
| 2014/0296962 A1 | 10/2014 | Cartledge et al. |
| 2014/0379067 A1 * | 12/2014 | Nguyen ................ A61F 2/2433 |
| | | 623/1.11 |
| 2016/0296730 A1 | 10/2016 | Zhou et al. |
| 2017/0014157 A1 | 1/2017 | Coyle et al. |
| 2017/0065415 A1 | 3/2017 | Rupp et al. |
| 2018/0153689 A1 | 6/2018 | Maimon et al. |
| 2018/0207395 A1 | 7/2018 | Bulman et al. |
| 2018/0256858 A1 * | 9/2018 | Zhou ................ A61M 25/0662 |

(56) References Cited

U.S. PATENT DOCUMENTS

2018/0344456 A1    12/2018  Barash et al.
2020/0139079 A1*   5/2020   Le .................... A61M 25/0662
2022/0379094 A1*   12/2022  Zhou .................... A61F 2/958

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |
| WO | 2016164079 A1 | 10/2016 |

\* cited by examiner

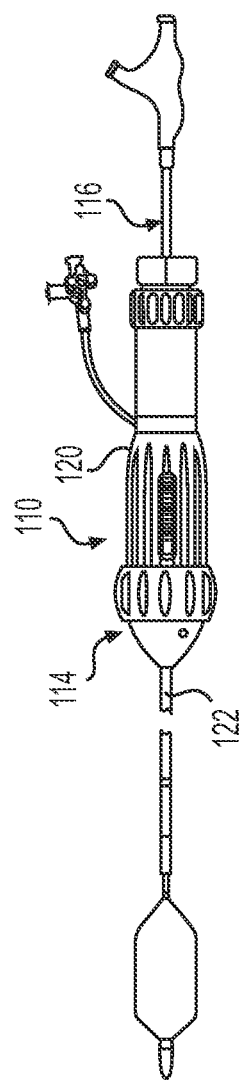
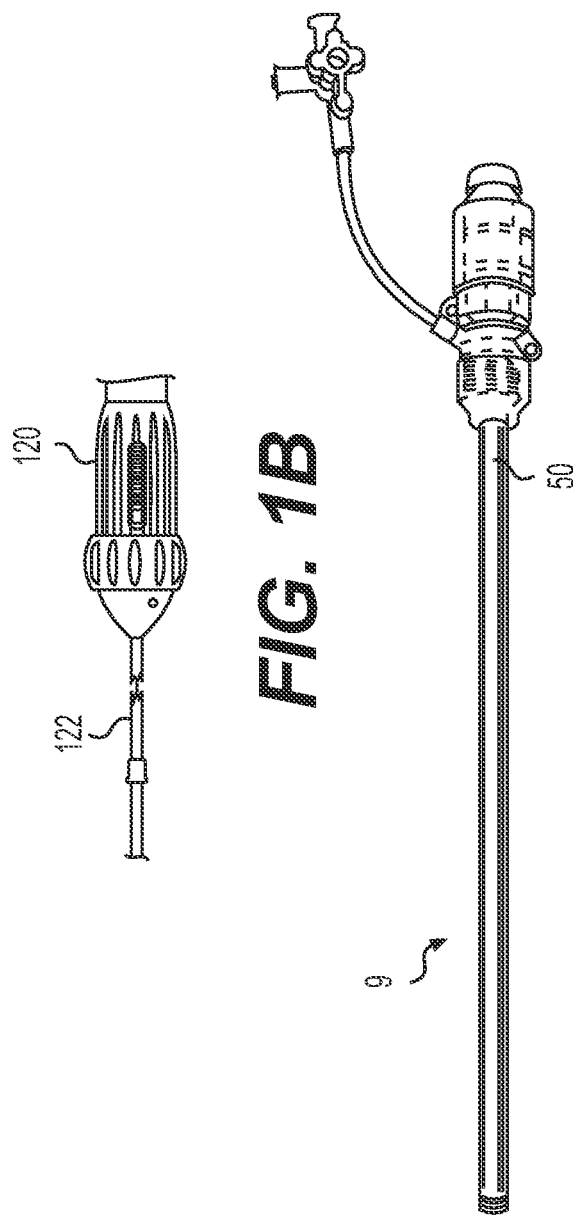
FIG. 1A
FIG. 1B
FIG. 1C

COMBINED INTRODUCER AND EXPANDABLE SHEATH

CROSS-REFERENCE TO RELATED APPLICATIONS

This application is a continuation of pending International Application No. PCT/US2019/064875, filed Dec. 6, 2019, which claims priority to and the benefit of U.S. Provisional Patent Application No. 62/778,698, filed Dec. 12, 2018, and entitled "Combined Introducer and Expandable Sheath." Each of the aforementioned applications is hereby incorporated by reference in its entirety.

FIELD

The present application concerns embodiments of a sheath for use with catheter-based technologies to introduce a prosthetic device, such as a heart valve or other implant, into the patient's vasculature.

BACKGROUND

Endovascular delivery catheter assemblies are used to implant prosthetic devices, such as a prosthetic heart valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques, including transcatheter delivery methods.

A sheath can be used to safely introduce a delivery apparatus into a patient's vasculature (e.g., the femoral artery). A sheath generally has an elongated sleeve that is inserted into the vasculature and a housing that contains one or more sealing valves that allow a delivery apparatus to be placed in fluid communication with the vasculature with minimal blood loss.

Radially expanding intravascular sheaths reduce the overall profile of the sheath to reduce risk of damage to the vessel. Some radially expanding sheaths have complex mechanisms, such as ratcheting mechanisms that maintain the shaft or sheath in an expanded configuration once a device with a larger diameter than the sheath's original diameter is introduced. Others may incorporate elasticity and folding to achieve expandability during passage of a medical device, followed by collapse after the passage of the medical device.

Despite the advances in expandable intravascular sheath technology, delivery and/or removal of prosthetic devices and other material to or from a patient still poses a risk to the patient. For example, accessing the vessel, such as the femoral artery, remains a challenge due to the relatively large profile of the sheath and delivery system that can cause longitudinal and radial tearing of the vessel during insertion. Conventional methods of accessing a vessel prior to introducing the sheath include dilating the vessel using multiple tapered introducers (also known as dilators) that progressively increase in diameter. This repeated insertion and vessel dilation can increase the amount of time the procedure takes, as well as the risk of damage to the vessel. The repeated insertion and vessel dilation can additionally dislodge calcified plaque within the vessels, posing an additional risk of clots caused by the dislodged plaque.

Thus, there remains a need for further improvements in sheaths for delivery of endovascular systems used for implanting heart valves and other prosthetic devices.

SUMMARY

The presently disclosed combined sheath and introducer (the introducer sheath) includes a rounded and tapered distal tip, a low inner diameter and thick radially folded tapered segments that extend the distance between the outer diameter and the inner diameter. The introducer sheath has a higher rigidity/durometer than conventional sheaths. As such, the introducer sheath can be used without a dilator because it will not buckle or bend when inserted into the vascular site of a patient.

An exemplary combined introducer and expandable sheath according to principles described herein thus may include an elongate inner member having a plurality of radially folded tapered segments in an unexpanded state extending in a longitudinal direction along a longitudinal axis, the inner member defining an inner lumen having an inner diameter; and an elongate outer elastomeric jacket extending at least partially over the inner member and having a spring bias toward the inner lumen of the inner member; wherein the inner member provides sufficient rigidity to the combined introducer and expandable sheath for insertion in a patient's vasculature. The inner member may define a central lumen which extends in the longitudinal direction. The plurality of radially folded tapered segments may unfold toward an inner surface of the outer elastomeric jacket to expand the inner diameter of the inner lumen upon insertion of a medical delivery device into the lumen. In an aspect, the elongate inner member is compressible against a portion of the inner surface of the outer elastomeric jacket to expand the inner diameter of the elongate inner member, for example, to an expanded configuration for passage of an implant. In another aspect, the inner member is compressible independent of the outer elastomeric jacket distal to the seal.

The combined introducer and expandable sheath may include a strain relief portion extending distally from the proximal end of the outer elastomeric jacket. The outer elastomeric jacket can be attached to the strain relief portion. The inner member may include a tapered and rounded distal tip. The inner member may have fixed position longitudinally with respect to the outer elastomeric jacket. In an aspect, the outer elastomeric jacket is fused to the inner member.

The inner lumen can be at least partially defined by inner surfaces of the radially folded tapered segments in an unexpanded state. The thickness t of a tapered segment measured in an unexpanded state, from an inner surface of the tapered segment to an outer surface of the tapered segment, is from 0.045 inches to 0.07 inches. In some embodiments of the combined introducer and expandable sheath, each radially folded tapered segment widens as it extends radially outward. A selected tapered segment can be connected to a first circumferentially adjacent tapered segment at an inner connection point and a second circumferentially adjacent tapered segment at an outer connection point. In an unexpanded state, the inner connection point can be positioned adjacent the inner lumen of the inner member and the outer connection point can be positioned adjacent an outer surface of the inner member. The inner and outer connection points can be thinner in a radial direction than the tapered segments of the inner member. In this way, the inner member of the combined introducer and expandable sheath thins and widens traveling along its circumference. A plurality of outwardly extending gaps can extend radially outward from the inner lumen (between adjacent tapered segments), and a plurality of inwardly extending gaps can radially inward from an outer surface of the inner member.

The inwardly and outwardly extending gaps each travel at least a portion of the length of the inner member.

According to principles described herein a method of delivering a prosthetic device may include positioning a combined introducer and expandable sheath within the a vascular site of a patient, the combined introducer and expandable sheath including an elongate inner member having a plurality of radially folded tapered segments in an unexpanded state extending in a longitudinal direction along a longitudinal axis, the inner member defining an inner lumen having an inner diameter; and an elongate outer elastomeric jacket extending at least partially over the inner member and having a spring bias toward the inner lumen of the inner member; wherein the inner member provides sufficient rigidity to the combined introducer and expandable sheath for insertion at the vascular site; introducing a prosthetic device into the inner lumen of the inner member; advancing the prosthetic device through the inner lumen such that the prosthetic device exerts a radially outward localized force on an inner surface of the inner member and locally unfolds the plurality of radially folded tapered segments of the inner member into an expanded configuration; and returning the inner member to an unexpanded state at the urging of the outer elastomeric jacket after the prosthetic device has passed out of the lumen. The method can further include positioning the combined introducer and expandable sheath without any prior dilation steps having been performed on the vascular site. The plurality of radially folded tapered segments can be unfolded toward an inner surface of the outer elastomeric jacket to expand the inner diameter of the lumen upon insertion of a medical delivery device in the lumen. In some embodiments, unfolding the plurality of radially folded tapered segments further comprises widening inwardly and outwardly extending gaps between adjacent tapered segments. Unfolding the plurality of radially folded tapered segments can further include bending the inner member at a plurality of inner connection points and a plurality of outer connection points.

DESCRIPTION OF DRAWINGS

FIGS. 1A-1C show side elevation views of a conventional expandable sheath (FIG. 1C) and a delivery apparatus for deployment through the sheath (FIGS. 1A-1B).

DETAILED DESCRIPTION

Figure 2:
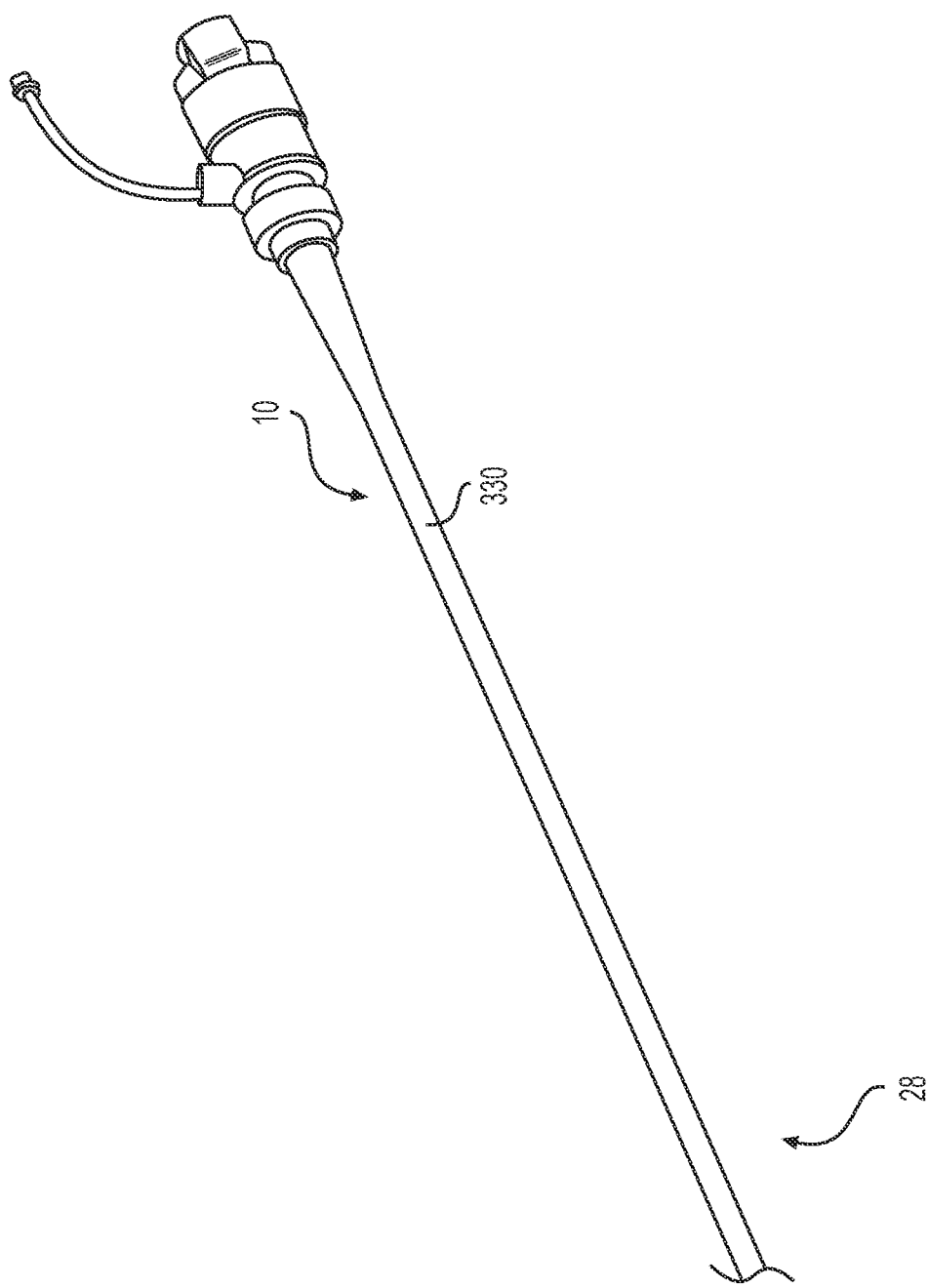
FIG. 2 shows a perspective view of a conventional expandable sheath.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device.

The term "tube" or "tubular" as used herein is not meant to limit shapes to circular cross-sections. Instead, tube or tubular can refer to any elongate structure with a closed-cross section and lumen extending axially therethrough. A tube may also have some selectively located slits or openings therein—although it still will provide enough of a closed structure to contain other components within its lumen(s).

As described above, current procedures for insertion of sheaths for delivery of prosthetic devices can be damaging to the vascular site. Part of the reason includes the use of introducers (also known as dilators), which are rigid, tapered, solid rods that are inserted into the vascular site to progressively widen the site in preparation for the introduction of the sheath. The repeated insertion of these dilators can cause damage to the vascular site and, in some cases, can dislodge plaques that can cause further complications during the procedure. Furthermore, expandable sheaths are being made with smaller diameters creating challenges for the expansion mechanism to be packed into smaller spaces.

Disclosed herein is a combined introducer and expandable sheath (hereinafter, an introducer sheath). The introducer sheath provides an expandable sheath that can be inserted without the need for preliminary dilation steps using conventional introducers. The unitary structure serves the purposes of both introducer and sheath, eliminating the time and risk involved in dilating the vessel. The wide radial folds extending the thickness of the wall of the inner member allow for a high degree of expansion. The distal region tapers to a rounded tip to facilitate dilation of the vascular site. The proximal region also tapers to mate with a hemostasis valve housing.

FIGS. 1A-1C illustrate a conventional delivery apparatus 110 and sheath 9 for delivering a prosthetic implant, such as a prosthetic heart valve, to a patient. It should be understood that the delivery apparatus 110 described herein is exemplary only, and that other similar delivery systems can of course be used with the disclosed introducer sheath 10. The delivery apparatus 110 illustrated herein generally includes a steerable guide catheter 114 and a balloon catheter 116 extending through the guide catheter 114. The guide catheter 114 and the balloon catheter 116 illustrated in FIGS. 1A-1B are adapted to slide longitudinally relative to each other to facilitate delivery and positioning of prosthetic heart valve at an implantation site in a patient's body. The guide catheter 114 includes a handle portion 120 and an elongated guide tube, or shaft, 122 extending from handle portion 120 (FIG. 1B).

FIG. 1C illustrates a conventional expandable sheath 9 that is used to introduce the delivery apparatus 110 and the prosthetic device into the patient's body. A conventional expandable sheath 9 has generally tubular configuration defining a central lumen to guide passage of the delivery system for the prosthetic heart valve. At a proximal end, the expandable sheath 9 includes a hemostasis valve that prevents leakage of pressurized blood. Generally, during use a distal end of the sheath 9 is passed into the vessel (such as a femoral artery) of the patient by sliding the lumen of sheath 9 over a previously inserted introducer (which may have the shape of a rigid, tapered rod). The introducer is then removed through the lumen of the sheath 9. The delivery apparatus 110 (with its implant) can then be inserted through the hemostasis valve, into the lumen of sheath 9, and advanced through the patient's vasculature where the implant is delivered and implanted within the patient.

In general, as described above, for insertion of the conventional sheath 9 into the patient's vessel, an introducer (also called a dilator) must be inserted into the vasculature prior to the sheath 9. The introducer provides sufficient rigidity not to buckle or bend during insertion, and the more flaccid conventional sheath 9 can then be inserted over the introducer and into the vessel. During a conventional procedure, the introducer is removed once the sheath 9 is inserted into the patient's vessel (prior to insertion of the delivery apparatus 110 through the sheath 9). According to principles described herein, a combined introducer and expandable sheath has a unitary structure that serves as both sheath and introducer, thus eliminating the preliminary steps of dilating the vascular site and removing the introducer before inserting the delivery apparatus.

Figure 3:
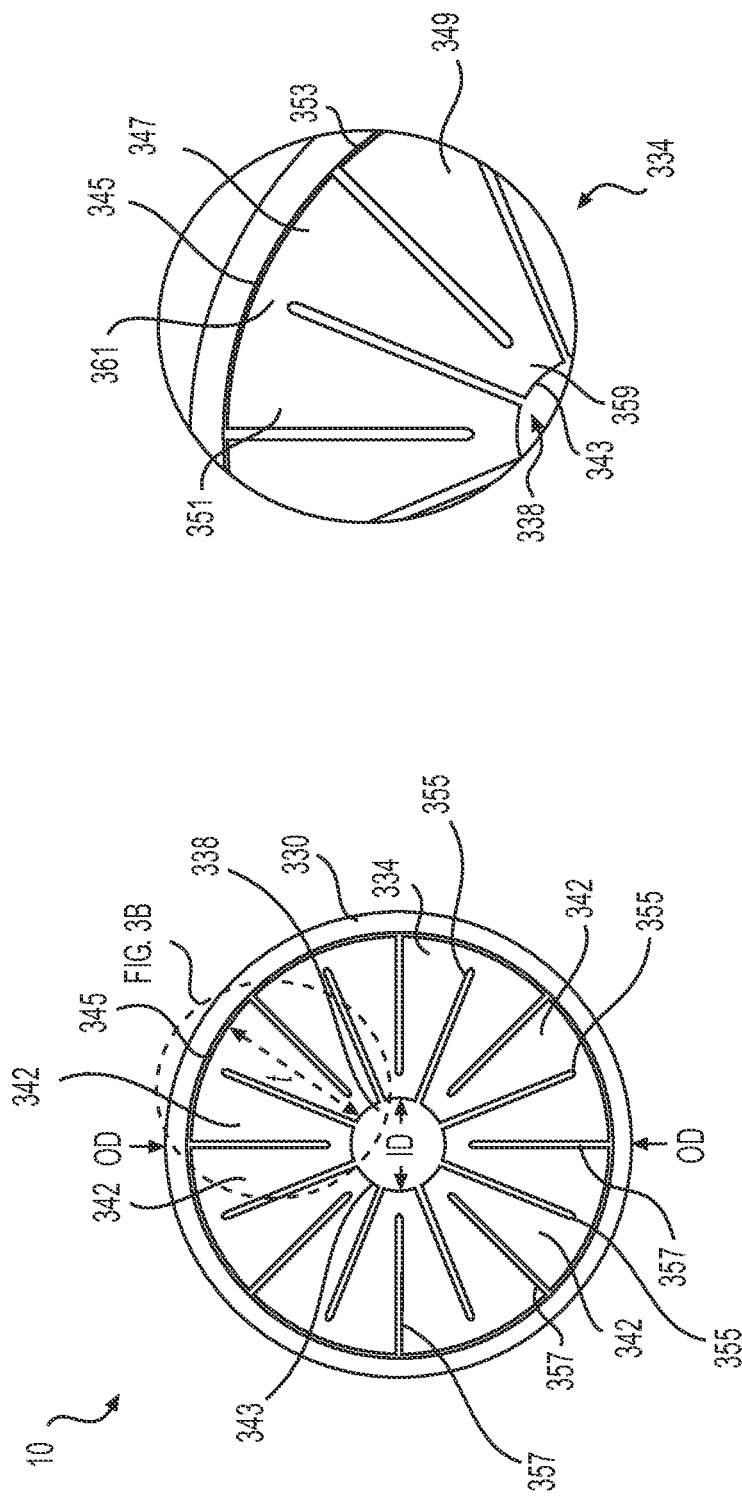
FIG. 3A shows a cross section of a combined introducer and an expandable sheath in an unexpanded state according to principles described herein.
FIG. 3B shows an enlarged section of FIG. 3A.
Figure 4:
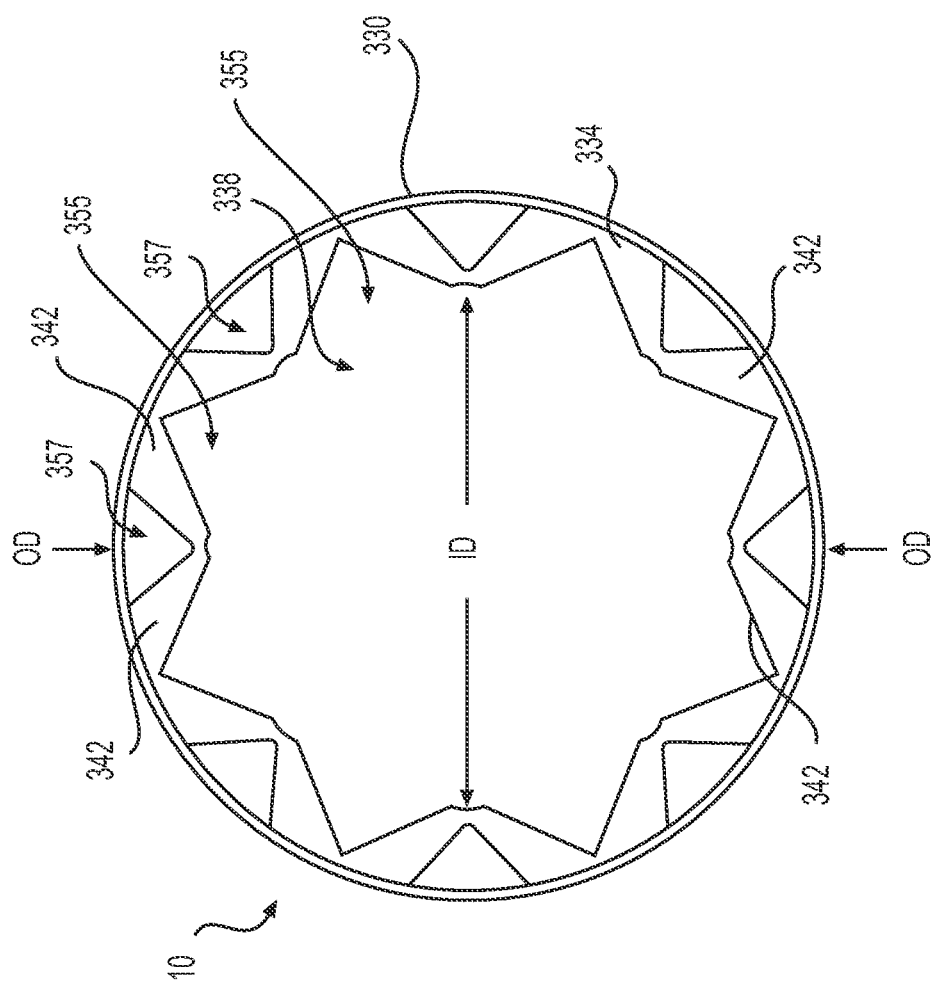
FIG. 4 shows a cross section of a combined introducer and an expandable sheath in an expanded state according to principles described herein.
Figure 5:
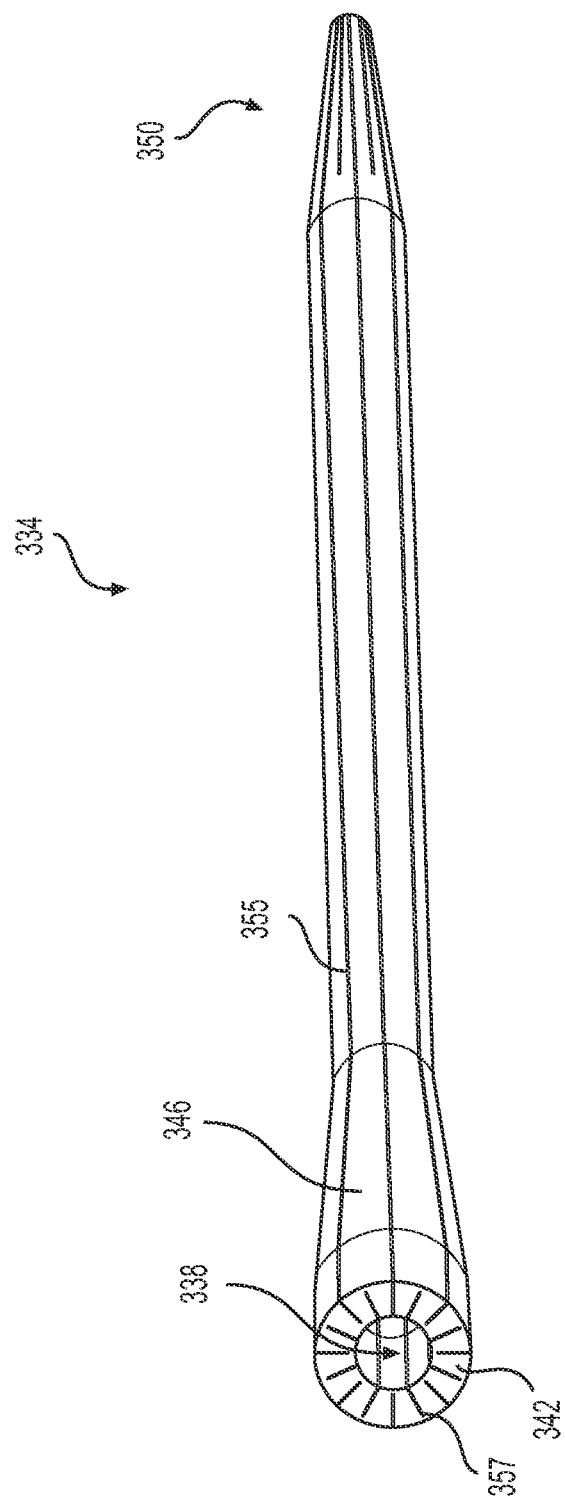
FIG. 5 shows an inner member of a combined introducer and an expandable sheath according to principles described herein.

In one embodiment, the combined introducer and expandable sheath 10 (hereinafter, the introducer sheath 10) includes and an outer elastomeric jacket 330 extending along the longitudinal axis of the sheath, as shown in FIG. 2. FIGS. 3A and 4 illustrate a cross section of an introducer sheath 10 in which the same structure serves as both the sheath and a dilator. FIG. 5 shows an embodiment of the inner member of introducer sheath 10 (without outer jacket elastomeric 330 for illustration purposes).

FIG. 3A illustrates a cross section the introducer sheath 10 in an unexpanded state. As illustrated, the introducer sheath 10 includes an outer elastomeric jacket 330 and an inner member 334 within the elastomeric jacket 330. In the unexpanded state, inner member 334 defines an inner lumen 338 having an inner diameter ID. In an exemplary embodiment, the unexpanded inner diameter of the inner member 334 (i.e., the diameter of inner lumen 338) may be about 0.04 inches (a size that is compatible with a guide wire having an outer diameter of about 0.038 inches). In an unexpanded state, the outer diameter OD of the introducer sheath 10, including elastomeric jacket 330, can be from about 0.13 inches to about 0.18 inches. In the expanded state (shown in FIG. 4), the inner diameter ID of the inner member 334 (the expanded ID) can be from about 0.28 inches to about 0.33 inches. This high expanded inner diameter ID is granted by the high inner surface area allotted by the many radial folds; in cross section, the full perimeter of the unexpanded inner surface of the inner member 334 (including the surface within the radial folds) is greater than the perimeter of circle having a diameter of 0.30 inches. In the expanded state, the outer diameter OD of the introducer sheath 10 can be from about 0.34 inches to about 0.37 inches.

In an unexpanded state, the inner member 334 comprises a plurality of radially folded tapered segments 342. The inner lumen 338 is at least partially defined by a plurality of inner surfaces 343 of the tapered segments 342. As shown in FIG. 3A, each tapered segment 342 widens as it extends radially outward (from an inner surface 343 of a tapered segment 342 to an outer surface 345 of a tapered segment 342). Generally, the thickness t of a tapered segment (as measured from inner surface 343 to outer surface 345 when the introducer sheath 10 is in an unexpanded state) can range from about 0.045 inches to about 0.07 inches. This thickness is relatively high as compared to conventional sheaths, which typically have a wall thickness of about 0.010 inches to about 0.020 inches. This relatively large thickness gives the introducer sheath 10 disclosed herein a greater columnar strength to help eliminate the need for an introducer/dilator during the insertion procedure. Furthermore, the relative thickness of the radial folds is high compared to current expandable sheaths that utilize folds as part of the expansion mechanism. This greater thickness of the radial folds allows for a much higher degree of expansion (greater difference between unexpanded outer diameter and expanded outer diameter), facilitating the design of smaller profile sheaths.

An enlarged portion of FIG. 3A is shown in FIG. 3B. As shown in FIG. 3B, a selected tapered segment 347 is connected to a first circumferentially adjacent tapered segment 349 at an inner connection point 359, which is positioned adjacent the inner lumen 338 defined by the inner member 334. The same selected tapered segment 347 is connected to a second circumferentially adjacent tapered segment 351 at an outer connection point 361, which is positioned adjacent the outer surface 353 of the inner member 334. The connection points 359, 361 are thinner in a radial direction than the tapered segments 342 of the inner member 334, such that the inner member 334 thins and widens traveling along its circumference (as shown, for example, in FIG. 4). In this way, the inner member 334 defines a plurality of outwardly extending gaps 355 that extend radially outward from inner lumen 338, as shown in FIG. 3A. The outwardly extending gaps 355 travel at least a portion of the length of inner member 334, as shown in FIG. 5. A plurality of inwardly extending gaps 357 extend radially inward from the outer surface of inner member 334, and also travel at least a portion of the length of the inner member 334, as shown in FIG. 3A and FIG. 5. Each of the outwardly and inwardly extending gaps 355, 357 are at least partially defined by two adjacent tapered segments 342. During expansion, the inner member 334 bends at the inner and outer connection points 359, 361 to cause tapered segments 342 to separate and widen the inwardly and outwardly extending gaps 355, 357, as shown in FIG. 4.

FIG. 4 illustrates a cross section of introducer sheath 10 in an expanded state. As illustrated, when expanded, the elastomeric jacket 330 thins and the radially folded tapered segments 342 of the inner member 334 unfold towards the elastomeric jacket 330 to expand/widen the lumen 338. The expansion is provided by the insertion of a medical delivery device. The device, for example, may be a transcatheter heart valve (THV) delivery device provided over a guide wire through the lumen of the inner member 334. The medical delivery device mechanically pushes open the tapered segments 342 of the inner member 334, as illustrated in FIG. 4. The outer elastomeric jacket 330 also expands to an increased outer diameter with the insertion of the medical device in the lumen 338 of the inner member 334. Upon removal of the medical device, the outer jacket material supplies sufficient elasticity to return the folded inner member 334 back to the unexpanded/folded state after THV passage and supply hemostasis for the inner member exterior channels.

FIG. 5 illustrates an inner member 334 of an introducer sheath 10 according to principles described herein. As illustrated in its unexpanded/folded state, the inner member 334 is substantially cylindrical and can be extruded with a proximal bump/taper 346. The proximal bump/taper 346 facilitates the mating of the introducer sheath 10 to the wider hemostasis valve housing during the manufacturing process. Furthermore, the ratio of the outer diameter to inner diameter at the bump/taper 346 region is higher than at other regions along the length of the introducer sheath 10. This higher OD/ID translates to more wall material (greater wall thickness t), which gives good force transmission down the length of the introducer sheath 10. At the distal end, inner member 334 may also include a tapered and rounded tip 350 to assist in dilation of the vasculature during introduction of the introducer sheath 10.

The inner member 334 may be fixed with respect to the outer elastomeric jacket or jacket or may "float" relative to the outer sheath. For example, the inner member 334 and the outer elastomeric jacket 330 may be attached, by, for example, adhesives or heat bonding, at fixed locations such that they do not move relative to one another or may be connected to one another. For example, the inner member 334 and the outer elastomeric jacket 330 may be attached at the tip 350 of the introducer sheath 10, or they may be attached along portions of the length of the introducer sheath 10.

The inner member 334 and the outer elastomeric jacket 330 may be formed independently or in an integral process. If formed independently, the elastomeric jacket 330 may be expanded by known means, the inner member 334 inserted into the elastomeric jacket 330 and the elastomeric jacket 330 allowed to contract around the inner member 334. The compressive force of the elastomeric jacket 330 around the inner member 334 may be sufficient to reduce movement between the elastomeric jacket 330 and the inner member 334 sufficiently to serve the functions described herein.

The material of inner member 334 has substantial column strength to provide rigidity to the elastomeric jacket 330 for catheter insertion, high lubricity for guide wire and THV passage, and high pliability so expansion force is low. For example, the inner member 334 may be made of a material such as high density polyethylene, fluoropolymers, Teflon or other material. In some embodiments, the inner member 334 can have a durometer of from about 45 D to about 65 D. Thus, the introducer sheath 10 provides sufficient rigidity to be able to be inserted through the skin of a patient and into the circulatory system. An alternative is to use a co-extruded inner member to get the desired properties in the locations required.

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above but should be determined only by a fair reading of the claims that follow.

What is claimed is:

1. A combined introducer and expandable sheath, comprising:
   an elongate inner member having a plurality of radially folded tapered segments in an unexpanded state extending in a longitudinal direction along a longitudinal axis, the inner member defining a longitudinally extending inner lumen having an inner diameter;
   an elongate outer elastomeric jacket extending at least partially over the inner member and having a spring bias toward the inner lumen of the inner member; and
   a plurality of outwardly extending gaps extending radially outward from the inner lumen and between adjacent tapered segments and a plurality of inwardly extending gaps extending radially inward from an outer surface of the inner member.

2. The combined introducer and expandable sheath of claim 1, wherein the plurality of radially folded tapered segments unfold toward an inner surface of the outer elastomeric jacket to expand the inner diameter of the inner lumen upon insertion of a prosthetic device in the inner lumen.

3. The combined introducer and expandable sheath of claim 1, wherein the inner member further includes a tapered and rounded distal tip.

4. The combined introducer and expandable sheath of claim 1, wherein the inner member has fixed position longitudinally with respect to the outer elastomeric jacket.

5. The combined introducer and expandable sheath of claim 1, wherein in an unexpanded state, the inner lumen is at least partially defined by inner surfaces of the plurality of radially folded tapered segments.

6. The combined introducer and expandable sheath of claim 1, wherein a thickness t of at least one of the plurality of radially folded tapered segments measured in the unexpanded state from an inner surface of the at least one tapered segment to an outer surface of the at least one tapered segment is from 0.045 inches to 0.07 inches.

7. The combined introducer and expandable sheath of claim 1, wherein each of the plurality of radially folded tapered segments widens as it extends radially outward.

8. The combined introducer and expandable sheath of claim 7, wherein each of the plurality of radially folded tapered segments is connected to a first circumferentially adjacent tapered segment of the plurality of radially folded tapered segments at an inner connection point and a second circumferentially adjacent tapered segment of the plurality of radially folded tapered segments at an outer connection point.

9. The combined introducer and expandable sheath of claim 8, wherein in the unexpanded state, the inner connection point is positioned adjacent the inner lumen of the inner member and the outer connection point is positioned adjacent an outer surface of the inner member.

10. The combined introducer and expandable sheath of claim 8, wherein the inner and outer connection points are thinner in a radial direction than the plurality of radially folded tapered segments.

11. The combined introducer and expandable sheath of claim 1, wherein the inner member thins and widens traveling along its circumference.

12. The combined introducer and expandable sheath of claim 1, wherein the inwardly and outwardly extending gaps each travel at least a portion of the length of the inner member.

13. A method of delivering a prosthetic device, the method comprising:
positioning a combined introducer and expandable sheath at a delivery site, the combined introducer and expandable sheath comprising:
an elongate inner member having a plurality of radially folded tapered segments in an unexpanded state extending in a longitudinal direction along a longitudinal axis, the inner member defining an inner lumen having an inner diameter;
an elongate outer elastomeric jacket extending at least partially over the inner member and having a spring bias toward the inner lumen of the inner member;
wherein the inner member provides rigidity to the combined introducer and expandable sheath during introduction to the delivery site;
introducing a prosthetic device into the inner lumen of the inner member;
advancing the prosthetic device through the inner lumen such that the prosthetic device exerts a radially outward localized force on an inner surface of the inner member;
locally unfolding the plurality of radially folded tapered segments of the inner member into an expanded configuration, wherein unfolding the plurality of radially folded tapered segments further comprises widening inwardly and outwardly extending gaps between adjacent tapered segments; and
returning the inner member to an unexpanded state at the urging of the outer elastomeric jacket after the prosthetic device has passed out of the lumen.

14. The method of delivering a prosthetic device according to claim 13, further comprising positioning the combined introducer and expandable sheath without any prior dilation steps having been performed at the delivery site.

15. The method of delivering a prosthetic device according to claim 13, wherein unfolding the plurality of radially folded tapered segments further comprises bending the inner member at a plurality of inner connection points and a plurality of outer connection points.

16. A combined introducer and expandable sheath, comprising:
an elongate inner member having a plurality of radially folded tapered segments in an unexpanded state extending in a longitudinal direction along a longitudinal axis, the inner member defining a longitudinally extending inner lumen having an inner diameter; and
an elongate outer elastomeric jacket extending at least partially over the inner member and having a spring bias toward the inner lumen of the inner member;
wherein a thickness t of at least one of the plurality of radially folded tapered segments measured in the unexpanded state from an inner surface of the at least one tapered segment to an outer surface of the at least one tapered segment is from 0.045 inches to 0.07 inches.

17. The combined introducer and expandable sheath of claim 16, wherein the plurality of radially folded tapered segments unfold toward an inner surface of the outer elastomeric jacket to expand the inner diameter of the inner lumen upon insertion of a prosthetic device in the inner lumen.

18. The combined introducer and expandable sheath of claim 16, wherein the inner member further includes a tapered and rounded distal tip.

19. The combined introducer and expandable sheath of claim 16, wherein the inner member has fixed position longitudinally with respect to the outer elastomeric jacket.

20. The combined introducer and expandable sheath of claim 16, wherein in an unexpanded state, the inner lumen is at least partially defined by inner surfaces of the plurality of radially folded tapered segments.

21. The combined introducer and expandable sheath of claim 16, wherein each of the plurality of radially folded tapered segments widens as it extends radially outward.

22. The combined introducer and expandable sheath of claim 21, wherein a each of the plurality of radially folded tapered segments is connected to a first circumferentially adjacent tapered segment of the plurality of radially folded tapered segments at an inner connection point and a second circumferentially adjacent tapered segment of the plurality of radially folded tapered segments at an outer connection point.

23. The combined introducer and expandable sheath of claim 22, wherein in the unexpanded state, the inner connection point is positioned adjacent the inner lumen of the inner member and the outer connection point is positioned adjacent an outer surface of the inner member.

24. The combined introducer and expandable sheath of claim 22, wherein the inner and outer connection points are thinner in a radial direction than the plurality of radially folded tapered segments.

25. The combined introducer and expandable sheath of claim 16, wherein the inner member thins and widens traveling along its circumference.

26. The combined introducer and expandable sheath of claim 16, further comprising a plurality of outwardly extending gaps extending radially outward from the inner lumen and between adjacent tapered segments and a plurality of inwardly extending gaps extending radially inward from an outer surface of the inner member, wherein the inwardly and outwardly extending gaps each travel at least a portion of the length of the inner member.

27. A method of delivering a prosthetic device, the method comprising:
   positioning a combined introducer and expandable sheath at a delivery site, the combined introducer and expandable sheath comprising:
      an elongate inner member having a plurality of radially folded tapered segments in an unexpanded state extending in a longitudinal direction along a longitudinal axis, the inner member defining an inner lumen having an inner diameter;
      an elongate outer elastomeric jacket extending at least partially over the inner member and having a spring bias toward the inner lumen of the inner member;
      wherein the inner member provides rigidity to the combined introducer and expandable sheath during introduction to the delivery site;
   introducing a prosthetic device into the inner lumen of the inner member;
   advancing the prosthetic device through the inner lumen such that the prosthetic device exerts a radially outward localized force on an inner surface of the inner member;
   locally unfolding the plurality of radially folded tapered segments of the inner member into an expanded configuration, wherein unfolding the plurality of radially folded tapered segments further comprises bending the inner member at a plurality of inner connection points and a plurality of outer connection points; and
   returning the inner member to an unexpanded state at the urging of the outer elastomeric jacket after the prosthetic device has passed out of the lumen.

28. The method of delivering a prosthetic device according to claim 27, further comprising positioning the combined introducer and expandable sheath without any prior dilation steps having been performed at the delivery site.

\* \* \* \* \*